United States Patent [19]

Yamamoto et al.

[11] Patent Number: 4,810,790
[45] Date of Patent: Mar. 7, 1989

[54] 5-FLUOROURACIL DERIVATIVES USEFUL AS CARCINOSTATIC SUBSTANCES

[75] Inventors: Yoshihiro Yamamoto; Kazuhiro Shimokawa, both of Settsu; Toru Yoshizawa, Osaka; Toshihiko Kawano, Ohtsu; Hiroyuki Iwai, Settsu, all of Japan

[73] Assignee: Daikin Industries Ltd., Osaka, Japan

[21] Appl. No.: 106,423

[22] Filed: Oct. 9, 1987

[30] Foreign Application Priority Data

Oct. 9, 1986 [JP] Japan .............................. 61-241118
May 6, 1987 [JP] Japan .............................. 62-110147

[51] Int. Cl.$^4$ .................................................. C07D 239/54
[52] U.S. Cl. ................................... 544/311; 544/313
[58] Field of Search ................... 544/311, 313; 514/274

[56] References Cited

FOREIGN PATENT DOCUMENTS

| 0193944 | 9/1986 | European Pat. Off. . | |
| 3098974 | 8/1978 | Japan | 544/311 |
| 4032487 | 3/1979 | Japan | 544/311 |
| 2854008 | 9/1979 | Japan | 514/274 |
| 5087721 | 7/1980 | Japan | 514/274 |
| 5136267 | 10/1980 | Japan | 544/311 |
| 63966 | 5/1981 | Japan . | |
| 0181075 | 9/1985 | Japan | 544/311 |
| 1524640 | 9/1978 | United Kingdom . | |

OTHER PUBLICATIONS

Gan to Kagakmyouhow, 8, No. 11(1981) pp. 1811–1820.

Ishikawa et al., CA85-192754y (1976), "1-carbamoyl-5-fluorouracils".
Ozaki et al., CA88-37728q (1978) "5-F-uracil derivatives, I. The Synthesis of 1-carbanroyl-5-fluorouracils".
Tokyo Kinzoku Kogyo Co. Ltd. CA95-150701e (1981) "Pyrinidine Derivatives".

Primary Examiner—Donald G. Daus
Assistant Examiner—Cecilia Shen
Attorney, Agent, or Firm—Birch, Stewart, Kolasch & Birch

[57] ABSTRACT

A novel 5-fluorouracil derivative of the formula:

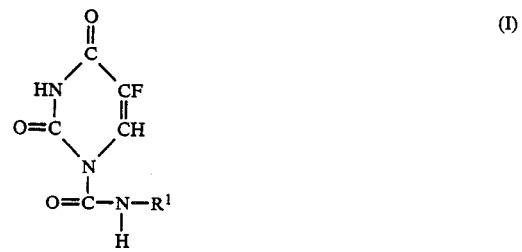

wherein $R^1$ is a fluorine-containing $C_1$–$C_{10}$ organic group which optionally contains sulfur, oxygen and/or nitrogen. The novel 5-fluorouracil derivative is useful as a carcinostatic substance, which has a high carcinostatic activity but which is less toxicity against digestive tract and causes less autonomic imbalance than other known 5-fluorouracil derivatives.

5 Claims, No Drawings

5-FLUOROURACIL DERIVATIVES USEFUL AS CARCINOSTATIC SUBSTANCES

BACKGROUND OF THE INVENTION

1. Field of the Invention

The present invention relates to novel 5-fluorouracil derivatives, which are useful as carcinostatic substances.

2. Discussion of Related Art

5-Fluorouracil is known as a antimetabolite having a broad-spectrum antitumor activity and used in clinical therapy. However, it is highly toxic when orally administered and particularly accompanied with side effects such as disorders in the gastrointestinal.

To solve such drawbacks of 5-fluorouracil, many derivatives of 5-fluorouracil have been proposed. One of the early developed derivatives is 1-(2-tetrahydrofuryl)-5-fluorouracil. Although this compound is less toxic, its carcinostatic activity is weak so that it is not a satisfactory carcinostatic substance (cf. "Gan to Kagakuryouhou" (Cancer and Chemotherapy), 8, No. 11, 1811 (1981)).

To maintain the strong activity on one hand and to decrease the toxicity of 5-fluorouracil on the other hand, studies of the derivatives of 5-fluorouracil have been made. As a result, for example, 1-hexylcarbamoyl-5-fluorouracil was developed. This derivative is more suitable than the previous derivatives for oral administration, since it has stronger carcinostatic activity and lower toxicity against the gastrointestinal. However, since the metabolites produced from 1-hexylcarbamoyl-5-fluorouracil by the oxidation of the hexyl group in a liver causes autonomic imbalances such as frequency of feces, heat sensation and pollakiuria which are not found in the use of other 5-fluorouracil derivatives, as a practical matter, this derivative should be used together with a tranquilizer (cf. Pharmacia, 16, No. 6, 524–527 (1980)).

SUMMARY OF THE INVENTION

An object of the present invention is to provide novel 5-fluorouracil derivatives which are useful as carcinostatic substances having high activity but less toxicity.

Another object of the present invention is to provide novel 5-fluorouracil derivatives which cause less side effects such as disorders in the digestive tracts and autonomic imbalance.

Accordingly, the present invention provides a novel derivative of the formula:

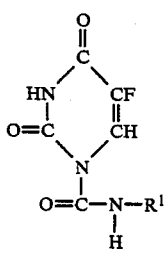
(I)

wherein $R^1$ is a fluorine-containing $C_1$–$C_{10}$ organic group which optionally contains sulfur, oxygen and/or nitrogen.

DETAILED DESCRIPTION OF THE INVENTION

Among the 5-fluorouracil derivatives (I) of the present invention, preferred are those in which $R^1$ is a group of the formula:

$$-(CH_2)_h-CH(R^2)-CF_3$$

wherein $R^2$ is hydrogen or a $C_1$–$C_4$ aliphatic group, and h is an integer of 0 to 4; a group of the formula:

$$-CH_2-(CR^3{}_2)_i-CHF_2$$

wherein $R^3$ is hydrogen or fluorine, and i is an integer of 0 to 5; or a group of the formula:

$$-(CH_2)_j-CHF(R^4)$$

wherein $R^4$ is hydrogen or methyl, and j is an integer of 1 to 4, since these preferred derivatives have large therapeutic indexes (TI) and/or causes less autonomic imbalance. Preferred examples of the group $R^1$ are —$CH_2CF_3$, —$(CH_2)_2CF_3$, —$(CH_2)_3CF_3$, —$(CH_2)_4CF_3$, —$(CH_2)_5CF_3$, —$CH_2CH(CH_3)CF_3$, —$CH_2CH(C_2H_5)CF_3$, —$CH_2CH(C_3H_7)$—$CF_3$, —$CH_2CH(C_4H_9)CF_3$, —$(CH_2)_2CH(CH_3)CF_3$, —$CH_2CHF_3$, —$(CH_2)_2$—$CHF_2$, —$(CH_2)_3CHF_2$, —$(CH_2)_4CHF_2$, —$(CH_2)_5CHF_2$, —$(CH_2)_4CH_2F$, —$(CH_2)_4CHFCH_3$ and —$(CH_2)_2NHC(=O)CH_2SCHF_2$. Among them, —$(CH_2)_2CF_3$, —$(CH_2)_3CF_3$, —$CH_2CH(CH_3)CF_3$, —$(CH_2)_2CH(CH_3)CF_3$ and —$(CH_2)_5CHF_2$ are more preferred.

The 5-fluorouracil derivative (I) of the present invention may be prepared by following methods (i) or (ii):

Method (i):

5-Fluorouracil is successively reacted, with phosgene ($COCl_2$) and a fluorine-containing amine of the formula:

$$NH_2R^1 \qquad (II)$$

wherein $R^1$ is the same as defined above, as follows:

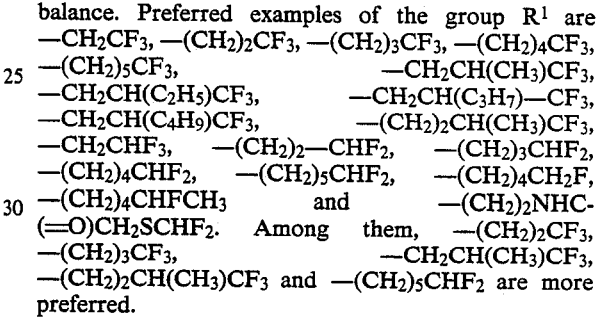

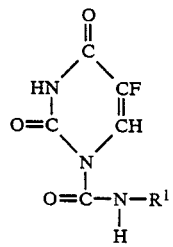

wherein $R^1$ is the same as defined above.

The first reaction of 5-fluorouracil with phosgene is effected by dissolving 5-fluorouracil in an organic base (e.g. pyridine, triethylamine and methylmorpholine)

and blowing 1.2 to 2 equivalents of phosgene in the solution of 5-fluorouracil with cooling at $-10°$ to $+10°$ C. The second reaction with the fluorine-containing amine is effected by adding 1 to 1.5 equivalents of said amine to the reaction mixture of 5-fluorouracil and phosgene at $-10°$ to $+10°$ C.

The fluorine-containing amine (II) may be prepared by, for example, converting a hydroxyl group and chlorine of a compound having the hydroxyl group and chlorine to fluorine and the amine group, respectively (cf. Bull. Chem. Soc. Jpn, 51, 1267 (1978) and Angew. Chem. Int. Ed., 7, 919 (1968)), or reducing a fluorine-containing primary amide with sodium borohydride or lithium aluminum hydride (cf. Tetrahedron Lett., 1969, 4555).

Method (ii):

A fluorine-containing carboxylic acid of the formula:

$$R^1COOH \qquad (III)$$

wherein $R^1$ is the same as defined above is reacted with diphenylphosphoryl azide to obtain an isocyanate of the formula:

$$OCN-R^1 \qquad (IV)$$

wherein $R^1$ is the same as defined above and reacting the isocyanate (IV) with 5-fluorouracil to obtain the 5-fluorouracil derivative (I) of the present invention.

The fluorine-containing carboxylic acid (III) can be prepared by the method described in J. Am. Chem. Soc., 76 3722 (1954).

When the fluorine-containing carboxylic acid (III), diphenylphosphoryl azide and 5-fluorouracil are mixed and heated in an organic solvent, the above two reactions proceed successively, it is not necessary to carry out these reactions stepwise. Examples of the organic solvent are pyridine, triethylamine, dimethylacetamide, dimethylformamide and mixtures thereof. Usually, the reaction temperature is from 10° to 110° C., and the reaction time is from 1 to 10 hours. The fluorine-containing carboxylic acid is used in an amount of 1 to 1.5 moles per mole of 5-fluorouracil, and diphenylphosphoryl azide is used in an amount of 1 to 1.5 moles per mole of 5-fluorouracil.

The present invention will be illustrated by following examples.

EXAMPLES 1-13

To a cold solution of 5-fluorouracil (2.6 g, 0.02 mole) in pyridine (50 ml) at $-3°$ to $+2°$ C., phosgene which is generated by dropping trichloromethyl chloroformate onto activated carbon (4 g, 0.02 mole) is introduced. After purging unreacted phosgene by blowing nitrogen in the mixture, a fluorine-containing amine shown in Table 1 (0.02 mole) is added to the mixture cooled at $-5°$ C. and stirred at the same temperature for one hour and then at room temperature for 30 minutes.

After concentrating the reaction mixture under reduced pressure, ethyl acetate (200 ml) and 1N hydrochloric acid (50 ml) are added and stirred. Materials precipitated are filtrated off. The filtrate (the ethyl acetate phase) is recovered and evaporated to dryness under reduced pressure followed by purification by column chromatography using silica gel.

The fluorine-containing amine used, the $R^1$ group contained in the product, a yield of the product, results of $^1$H- and $^{19}$F-NMR analyses of the product, ILS (%) and TI are shown in Table 1.

The ILS and TI have common meanings in this field and are measured according to the methods described in Chem. Pharm. Bull., 26, No. 1, 161-165 (1978) in which used are BDF type mice (female) (5 mice per group, an average weight of $16\pm2$ g) inplanted by $1\times10^5$ cells of lymphocytic leukemia L-1210 (National Cancer Institute type) and the product is orally administered.

EXAMPLES 14-17

To a mixture of dimethylformamide (15 ml), 5-fluorouracil (1 g, 7.7 mmol), diphenylphosphoryl azide (2.2 g, 8 mmol) and triethylamine (5.1 g, 50 mmol), a fluorine-containing carboxylic acid shown in Table 2 (8 mmol) is added and reacted at 80° C. for 2 hours.

After cooling, the reaction mixture is concentrated under reduced pressure. To the concentrated mixture, ethyl acetate (100 ml) and 1N hydrochloric acid (50 ml) are added and stirred. Materials precipitated are filtrated off. The filtrate (the ethyl acetate phase) is recovered and evaporated to dryness under reduced pressure followed by purification by column chromatography using silica gel with a mixed solvent of chloroform and ethanol in a volume ratio of 10:1. The fluorine-containing carboxylic acid, the $R^1$ group contained in the product, a yield of the product, results of $^1$H- and $^{19}$F-NMR analyses of the product, ILS (%) and TI are shown in Table 2.

As a solvent in the NMR analyses of the compounds, CDCl$_3$ is used in Examples 6, 8, 10, 11, 13, 16 and 17, and (CD$_3$)$_2$SO is used in other Examples. In $^{19}$F-NMR, trifluoroacetic acid is an external standard.

For evaluation of suppression of autonomic imbalance by the compound of the present invention, according to the descriptions of "Rinsho-yakuri" (Clinical pharmacology), 11, No. 1, 17 and 27 (1980), (1) action on neutrons in a pretaminar part of the optic nerve which is a center for regulation of the body temperature of rats and outside said part (a degree of caumesthesia) and (2) action on bladder movement of cats (frequency of uresiesthesia) are examined. From the results of these examinations, the compound having the $R^1$ group selected from the group consisting of $-(CH_2)_2-CF_3$, $-(CH_2)_3CF_3$, $-CH_2CH(CH_3)CF_3$, $-(CH_2)_2CH(CH_3)CF_3$ and $-(CH_2)_4CHF_2$ are found to have better effects.

COMPARATIVE EXAMPLES 1 AND 2

With a compound (I) wherein $R^1$ is $-(CH_2)_5CH_3$ (Comparative Example 1) or $-CH_2(CF_2)_2CF_3$ (Comparative Example 2), ILS and TI are measured. The results are shown in Table 3.

TABLE 1

| Example | F-containing amine | $R^1$ group | Yield (%) | $^1$H—NMR (ppm) | $^{19}$F—NMR | ILS (%) (Dose[1]) | TI |
|---|---|---|---|---|---|---|---|
| 1 | NH$_2$CH$_2$CF$_3$ | —CH$_2$CF$_3$ | 52 | 4–4.4 (2H, m), 8.45 (1H, d, J=7 Hz), 9.62 (1H, m), 12.4 (1H, bs) | −8.0 (3F, t, J=8.6 Hz) 85.8 (1F, d, J=7 Hz) | 79 (100) | 2.5 |
| 2 | NH$_2$(CH$_2$)$_3$—CF$_3$ | —(CH$_2$)$_3$—CF$_3$ | 62 | 1.7–2.05 (2H, m), 2.15–2.6 (2H, m), 3.3–3.65 (2H, m), 8.5 (1H, d, J=7 Hz), | −13.8 (3F, t, J=11.4 Hz), 86.9 (1F, d, J=7.1 | 55 (100) | 10.0 |

TABLE 1-continued

| Example | F-containing amine | R¹ group | Yield (%) | ¹H—NMR (ppm) | ¹⁹F—NMR | ILS (%) (Dose[1]) | TI |
|---|---|---|---|---|---|---|---|
| 3 | NH$_2$(CH$_2$)$_2$—CH(CH$_3$)CF$_3$ | —(CH$_2$)$_2$—CH(CH$_3$)—CF$_3$ | 72 | 9.35 (1H, m), 12.5 (1H, bs) 1.25 (3H, d, J=7.1 Hz), 1.4-2.1 (3H, m), 3.4-3.7 (2H, m), 8.5 (1H, d, J=7.5 Hz), 9.25-9.45 (1H, m), 12.4 (1H, bs) | −6.6 (3F, d, J=11.5 Hz), 86.9 (1F, d, J=7 Hz) | 76 (100) | 5.0 |
| 4 | NH$_2$CH$_2$CHF$_2$ | —CH$_2$CHF$_2$ | 56 | 3.85 (2H, m), 6.3 (1H, tt, J=5.7 Hz, J=57 Hz), 8.55 (1H, d, J=8.5 Hz), 9.55 (1H, m), 12.5 (1H, bs) | 44.2 (2F, dt, J=17 Hz, J=57 Hz), 86.1 (1F, d, J=7.1 Hz) | 59 (100) | 5.0 |
| 5 | NH$_2$(CH$_2$)$_4$—CHF$_2$ | —(CH$_2$)$_4$—CHF$_2$ | 61 | 1.4-2.1 (4H, m), 2.5-2.8 (2H, m), 3.3-3.6 (2H, m), 5.85 (1H, tt, J=5.7 Hz, J=57.1 Hz), 8.45 (1H, d, J=7.1 Hz), 9.35 (1H, bs), 12.3 (1H, bs) | 37.2 (2F, dt, J=17 Hz, J=57 Hz), 84.3 (1F, d, J=7.1 Hz) | 35 (200) | 3.0 |
| 6 | NH$_2$(CH$_2$)$_5$—CHF$_2$ | —(CH$_2$)$_5$—CHF$_2$ | 61 | 1.2-2.05 (8H, m), 3.5-3.6 (2H, q, J=5.7 Hz), 5.85 (1H, tt, J=5.4 Hz, J=57 Hz), 8.5 (1H, d, J=7 Hz), 9.05 (2H, bs) | 37.2 (2F, dt, J=17 Hz, J=57 Hz), 83.4 (1F, m) | 58 (300) | 10.0 |
| 7 | NH$_2$CH$_2$CF$_2$—CF$_2$H | —CH$_2$CF$_2$—CHF$_2$ | 45 | 3.6-4.4 (2H, m), 6.5 (1H, tt, J=51 Hz, 5.7 Hz), 8.5 (1H, d, J=7.1 Hz), 9.6 (1H, m), 12.5 (1H, bs) | 85.9 (1F, d, J=8.5 Hz), 59.7 (2F, m), 43.7-44.3 (2F, m) | 57 (200) | 3.6 |
| 8 | NH$_2$CH$_2$(CF$_2$—CF$_2$)$_2$H | —CH$_2$(CF$_2$—CF$_2$)$_2$H | 50 | 3.95-4.2 (2H, m), 6.1 (1H, tt, J=51 Hz, 5.7 Hz), 8.5 (1H, d, J=5.7 Hz), 8.65 (1H, bs), 9.55 (1H, bs) | 82.0 (1F, d, J=5.7 Hz), 39.3 (2F, m), 46.4 (2F, m), 50.8 (2F, m), 58.3 (2F, m) | 62 (200) | 3.3 |
| 9 | NH$_2$CH$_2$(CF$_2$—CF$_2$)$_3$H | —CH$_2$(CF$_2$—CF$_2$)$_3$H | 48 | 4-4.6 (2H, m), 7.3 (1H, tt, J=51 Hz, 5.7 Hz), 8.5 (1H, d, J=8.3 Hz), 9.7 (1H, m), 12.5 (1H, bs) | 85.7 (1F, d, J=7.1 Hz), 38.8 (2F, m), 43.4 (2F, m), 44.7 (4F, m), 50.4 (2F, m), 59.8 (2F, m) | 29 (100) | — |
| 10 | NH$_2$(CH$_2$)$_4$—CHFCH$_3$ | —(CH$_2$)$_4$—CHFCH$_3$ | 60 | 1.2-1.8 (10H, m), 3.42 (2H, t, J=5.7 Hz), 8.43 (1H, d, J=6 Hz), 8.8-9.1 (2H, bm), | 83.5 (1F, d, J=8.6 Hz), 94.4 (1F, m) | 54 (200) | 3.0 |
| 11 | NH$_2$(CH$_2$)$_4$—CH$_2$F | —(CH$_2$)$_4$—CH$_2$F | 56 | 1.3-2 (6H, m), 3.4 (2H, t, J=5.7 Hz), 4.45 (2H, dt, J=46 Hz, 5.7 Hz), 8.45 (1H, d, J=6 Hz), 8.8-9.3 (2H, bm) | 83.5 (1F, d, J=5.7 Hz), 139.9 (1F, tt, J=46 Hz, 23 Hz) | 51 (100) | 3.5 |
| 12 | NH$_2$(CH$_2$)$_5$—CF$_3$ | —(CH$_2$)$_5$—CF$_3$ | 53 | 1.3-1.9 (6H, m), 2.0-2.3 (2H, m), 3.3-3.5 (2H, m), 8.5 (1H, d, J=6 Hz), 8.6 (1H, bs), 9.1 (1H, bs) | −11.5 (3F, t, J=11.5 Hz), 84.2 (1F, d, J=7 Hz) | 60 (200) | 3.5 |
| 13 | NH$_2$CH$_2$CH$_2$—NHC(=O)CH$_2$—SCF$_2$H | —CH$_2$CH$_2$—NHC(=O)—CH$_2$SCHF$_2$ | 60 | 3.4-3.8 (6H, m), 7.55 (1H, t, J=57 Hz), 8.5 (1H, m), 8.6 (1H, d, J=8.5 Hz), 9.4 (1H, m), 12.55 (1H, bs) | 15.2 (2F, d, J=57 Hz), 86.6 (1F, d, J=5.7 Hz) | 53 (300) | 3.0 |

Note: [1]mg/kg/day.

TABLE 2

| Example | F-containing carboxylic acid | R¹ group | Yield (%) | ¹H—NMR (ppm) | ¹⁹F—NMR | ILS (%) (Dose[1]) | TI |
|---|---|---|---|---|---|---|---|
| 14 | CF$_3$CH$_2$CH$_2$—COOH | —CH$_2$CH$_2$—CF$_3$ | 48 | 2.55-2.95 (2H, m), 3.6-3.85 (2H, m), 8.6 (1H, d, J=7.1 Hz), 9.5 (1H, m), 12.5 (1H, bs) | −14.7 (3F, t, J=11.5 Hz), 86.4 (1F, d, J=7.5 Hz) | 85 (100) | 7.1 |
| 15 | CF$_3$CH(CH$_3$)—CH$_2$COOH | —CH$_2$CH—(CH$_3$)CF$_3$ | 65 | 1.2 (3H, d, J=7.1 Hz), 3.2-3.85 (3H, m), 8.45 (1H, d, J=7.5 Hz), 9.5 (1H, m), 12.55 (1H, bs) | −7.2 (3F, d, J=8.5 Hz), 84.7 (1F, d, J=7.5 Hz) | 62 (300) | 12.0 |
| 16 | CF$_3$CH(CH$_2$—CH$_3$)CH$_2$COOH | —CH$_2$CH—(CH$_2$CH$_3$)CF$_3$ | 52 | 1.1 (3H, t, J=8.5 Hz), 1.5-2.1 (3H, m), 3.5-3.8 (2H, m), 8.5 (1H, d, J=7.5 Hz), 8.6 (1H, bs), 9.3 (1H, bs) | −9.1 (3F, d, J=8.6 Hz), 82.9 (1F, d, J=7.1 Hz) | 40 (100) | 3.0 |
| 17 | CF$_3$CH(CH$_2$—CH$_2$CH$_2$CH$_3$)CH$_2$COOH | —CH$_2$CH—(CH$_2$CH$_2$—CH$_2$CH$_3$)CF$_3$ | 45 | 0.95 (3H, t, J=5.7 Hz), 1.2-1.9 (6H, m), 2.4 (1H, bs), 3.55-3.75 (2H, m), 8.5 (1H, d, J=7.5 Hz), 9.1 (1H, bs), 9.35 (1H, m) | −8.9 (3F, d, J=11.4 Hz), 82.9 (1F, d, J=14.3 Hz) | 53 (100) | 2.7 |

TABLE 3

| Comparative Example No. | ILS (%) (Dose: mg/kg/day) | TI |
|---|---|---|
| 1 | 70 (300) | 4.3 |
| 2 | 61 (100) | 2.0 |

What is claimed is:

1. A 5-fluorouracil derivative of the formula:

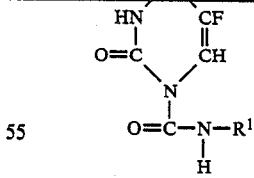

wherein R¹ is is selected from the group consisting of —(CH$_2$)$_3$CF$_3$, —(CH$_2$)$_5$CHF$_2$, —CH$_2$CH(CH$_3$)CF$_3$ and —CH$_2$CH$_2$CF$_3$.

2. The 5-fluorouracil derivative according to claim 1, wherein R¹ is —(CH$_2$)$_3$CF$_3$.

3. The 5-fluorouracil derivative according to claim 1, wherein R¹ is —(CH$_2$)$_5$CHF.

4. The 5-fluorouracil derivative according to claim 1, wherein R¹ is —CH$_2$CH(CH$_3$)CF$_3$.

5. The 5-fluorouracil derivative according to claim 1, wherein R¹ is —CH$_2$CH$_2$CF$_3$.

* * * * *